United States Patent
Barias et al.

(10) Patent No.: US 12,180,129 B2
(45) Date of Patent: Dec. 31, 2024

(54) USE OF DIVIDED WALL TECHNOLOGY TO PRODUCE HIGH PURITY METHANOL

(71) Applicant: LUMMUS TECHNOLOGY LLC, Bloomfield, NJ (US)

(72) Inventors: Rosette Barias, Spring, TX (US); Alejandro Maurer, Bloomfield, NJ (US)

(73) Assignee: Lummus Technology LLC, Houston, TX (US)

( * ) Notice: Subject to any disclaimer, the term of this patent is extended or adjusted under 35 U.S.C. 154(b) by 857 days.

(21) Appl. No.: 17/275,015

(22) PCT Filed: Sep. 11, 2019

(86) PCT No.: PCT/US2019/050553
§ 371 (c)(1),
(2) Date: Mar. 10, 2021

(87) PCT Pub. No.: WO2020/055963
PCT Pub. Date: Mar. 19, 2020

(65) Prior Publication Data
US 2022/0064078 A1   Mar. 3, 2022

Related U.S. Application Data

(60) Provisional application No. 62/730,456, filed on Sep. 12, 2018.

(51) Int. Cl.
*C07C 1/22* (2006.01)
*B01D 3/14* (2006.01)
(Continued)

(52) U.S. Cl.
CPC ............... *C07C 1/22* (2013.01); *B01D 3/141* (2013.01); *B01D 3/143* (2013.01);
(Continued)

(58) Field of Classification Search
None
See application file for complete search history.

(56) References Cited

U.S. PATENT DOCUMENTS

| | | |
|---|---|---|
| 3,121,124 A | 2/1964 | Verdol |
| 3,170,000 A | 2/1965 | Verdol |
| (Continued) | | |

FOREIGN PATENT DOCUMENTS

| | | |
|---|---|---|
| CN | 102190559 A | 9/2011 |
| EP | 2660231 A1 | 11/2013 |

OTHER PUBLICATIONS

International Search Report issued in International Application No. PCT/US2019/050553 dated Dec. 26, 2019 (4 pages).
(Continued)

*Primary Examiner* — Medhanit W Bahta
(74) *Attorney, Agent, or Firm* — Osha Bergman Watanabe & Burton LLP

(57) ABSTRACT

Methods and systems for producing high purity methanol and isobutene from crude MTBE feed using multiple divided wall columns are provided. The methods can include purifying the MTBE, dissociating the MTBE to produce isobutene and methanol, purifying the isobutene and recovering/purifying methanol.

14 Claims, 4 Drawing Sheets

(51) Int. Cl.
*B01D 11/04* (2006.01)
*C07C 1/20* (2006.01)
*C07C 7/04* (2006.01)
*C07C 7/08* (2006.01)
*C07C 29/10* (2006.01)
*C07C 29/58* (2006.01)
*C07C 29/80* (2006.01)
*C07C 29/84* (2006.01)
*C07C 41/06* (2006.01)
*C07C 41/42* (2006.01)

(52) U.S. Cl.
CPC ............ *B01D 11/0492* (2013.01); *C07C 1/20* (2013.01); *C07C 7/04* (2013.01); *C07C 7/08* (2013.01); *C07C 29/10* (2013.01); *C07C 29/58* (2013.01); *C07C 29/80* (2013.01); *C07C 29/84* (2013.01); *C07C 41/06* (2013.01); *C07C 41/42* (2013.01); *C07C 2531/08* (2013.01)

(56) References Cited

U.S. PATENT DOCUMENTS

| | | | |
|---|---|---|---|
| 3,634,534 | A | 1/1972 | Haunschild |
| 3,634,535 | A | 1/1972 | Haunschild |
| 4,232,177 | A | 11/1980 | Smith, Jr. |
| 4,320,232 | A | 3/1982 | Volkamer et al. |
| 7,439,413 | B2 * | 10/2008 | Malzkorn ................ C07C 1/20 585/809 |
| 2011/0118523 | A1 | 5/2011 | Winterberg et al. |
| 2012/0142985 | A1 | 6/2012 | Winterberg et al. |
| 2015/0251968 | A1 | 9/2015 | Brianti et al. |

OTHER PUBLICATIONS

Written Opinion issued in International Application No. PCT/US2019/050553 dated Dec. 26, 2019 (9 pages).

* cited by examiner

USE OF DIVIDED WALL TECHNOLOGY TO PRODUCE HIGH PURITY METHANOL

FIELD OF DISCLOSURE

Embodiments disclosed herein relate to processes and systems for co-producing isobutene and a high purity methanol product streams.

BACKGROUND

With the increasing demand for isobutene, the dissociation of methyl tertiary butyl ether (MTBE) for isobutene using a suitable catalyst is a relatively clean process compared to the cold acid treatment by which high purity isobutene may be obtained. Thus, the dissociation of MTBE is viable and economic. Furthermore, the cold acid process not only requires large amounts of energy, but is highly corrosive because of the sulfuric acid used. The use of cationic resin catalysts or other catalyst such as phosphoric acid supported on silica gel, alumina, supported metal sulfates for the dissociation require less energy and are substantially free of corrosion.

The reaction to produce MTBE is known to be reversible, i.e., the MTBE will dissociate to produce methanol and isobutene that were originally combined to produce the MTBE. For example, U.S. Pat. Nos. 3,121,124; 3,170,000; 3,634,534; 3,634,535; 4,232,177 and 4,320,232 disclose the dissociation of alkyltertiary alkyl ethers using ion exchange resin catalysts.

The use of acid cation exchange resins in the past for the dissociation of methyl tertiary butyl ether has been demonstrated, i.e., U.S. Pat. No. 3,121,124 (Verdol) using a gel type catalyst (Dowex 50) and U.S. Pat. No. 4,232,177 (Smith) used a macroreticular catalyst (Amberlyst 15) in a catalytic distillation process. The dissociation of MTBE will produce a stream containing isobutene, methanol, and some oxygenated compounds and polymer impurities.

SUMMARY OF INVENTION

The product stream resulting from MTBE decomposition, as noted above, includes various impurities. Further, the products may form azeotropes. Each of these may make the desired separations into high purity product streams more difficult.

Embodiments herein are directed toward systems and processes to co-produce a high purity methanol stream along with a targeted isobutene product.

In one aspect, embodiments herein are directed toward systems for producing isobutene and a high purity methanol product. The systems may include a system for the production of isobutene, the process comprising a first fractionation system which receives a feed stream comprising crude MTBE, and which produces an MTBE product stream comprising at least 94 wt % MTBE and a heavies stream; a first reactor configured for contacting the MTBE product stream with a catalyst to provide an effluent comprising isobutene and methanol; an extraction unit configured for contacting the effluent comprising isobutene and methanol with one or more extractants to produce an extractant/methanol stream and a mixed isobutene stream; a second fractionation system which receives the mixed isobutene stream, and which produces a stream comprising isobutene comprising at least 95 wt % isobutene; and a third fractionation system which receives the extractant/methanol stream, and which produces a methanol stream comprising at least 95 wt % methanol, a lights fraction, and a heavies fraction comprising extractant.

In one aspect, embodiments herein are directed toward processes for producing isobutene and a high purity methanol product. The processes may be a process for the coproduction of isobutene and high purity methanol, the process comprising separating a feed stream comprising crude MTBE in a first fractionation system to recover an MTBE product stream comprising at least 94 wt % MTBE, and to recover a heavies stream; contacting the MTBE product stream with a catalyst to provide an effluent comprising isobutene and methanol; contacting the effluent comprising isobutene and methanol with one or more extractants to produce an extractant/methanol stream and a mixed isobutene stream; feeding the mixed isobutene stream into a second fractionation system to recover a stream comprising isobutene comprising at least 95 wt % isobutene; and feeding the extractant/methanol stream into a third fractionation system to recover a lights fraction, a methanol product stream comprising at least 95 wt % methanol and a heavies fraction comprising the extractant.

In another embodiment, the process may be a process for the coproduction of isobutene and high purity methanol, the process comprising separating a feed stream comprising crude MTBE in a first fractionation system to recover an MTBE product stream comprising at least 94 wt % MTBE, and to recover a heavies stream; contacting the MTBE product stream with a catalyst to provide an effluent comprising isobutene and methanol; contacting the effluent with one or more extractants to produce an extractant/methanol stream and a mixed isobutene stream; feeding the mixed isobutene stream into a second fractionation system to recover a stream comprising isobutene comprising at least 95 wt % isobutene; and feeding the extractant/methanol stream into a third fractionation system comprising a divided wall distillation column to recover an overheads fraction, a methanol side draw product stream comprising at least 95 wt % methanol and a bottoms stream comprising the extractant.

In yet other embodiments, the process me be a process for the coproduction of isobutene and high purity methanol, the process comprising separating a feed stream comprising crude MTBE, C4s, C5s, diisobutene (DIB), tertiary butyl alcohol (TBA) and 2-methoxybutane (MSBE) in a first fractionation system to recover an MTBE product stream comprising at least 94 wt % MTBE, and to recover a heavies stream comprising a mixture of MTBE, tert-butyl alcohol (TBA), and 2-methoxybutane (MSBE); contacting the MTBE product stream with a catalyst to provide an effluent comprising isobutene, methanol, and residual MTBE; contacting the effluent with one or more extractants to produce an extractant/methanol stream and a mixed isobutene/MTBE stream; feeding the mixed isobutene/MTBE stream into a second fractionation system to recover a stream comprising isobutene comprising at least 94 wt % isobutene and a heavies stream comprising MTBE/isobutene; recycling the heavies stream comprising MTBE/isobutene to the first fractionation system; feeding the extractant/methanol stream into a third fractionation system comprising a divided wall distillation column to recover an overheads fraction, a methanol side draw product stream comprising at least 95 wt % methanol and a bottoms stream comprising residual MTBE, methanol, and the extractant; and recycling the bottoms stream comprising residual MTBE, methanol, and the extractant to the first fractionation system.

DETAILED DESCRIPTION

Figure 1:
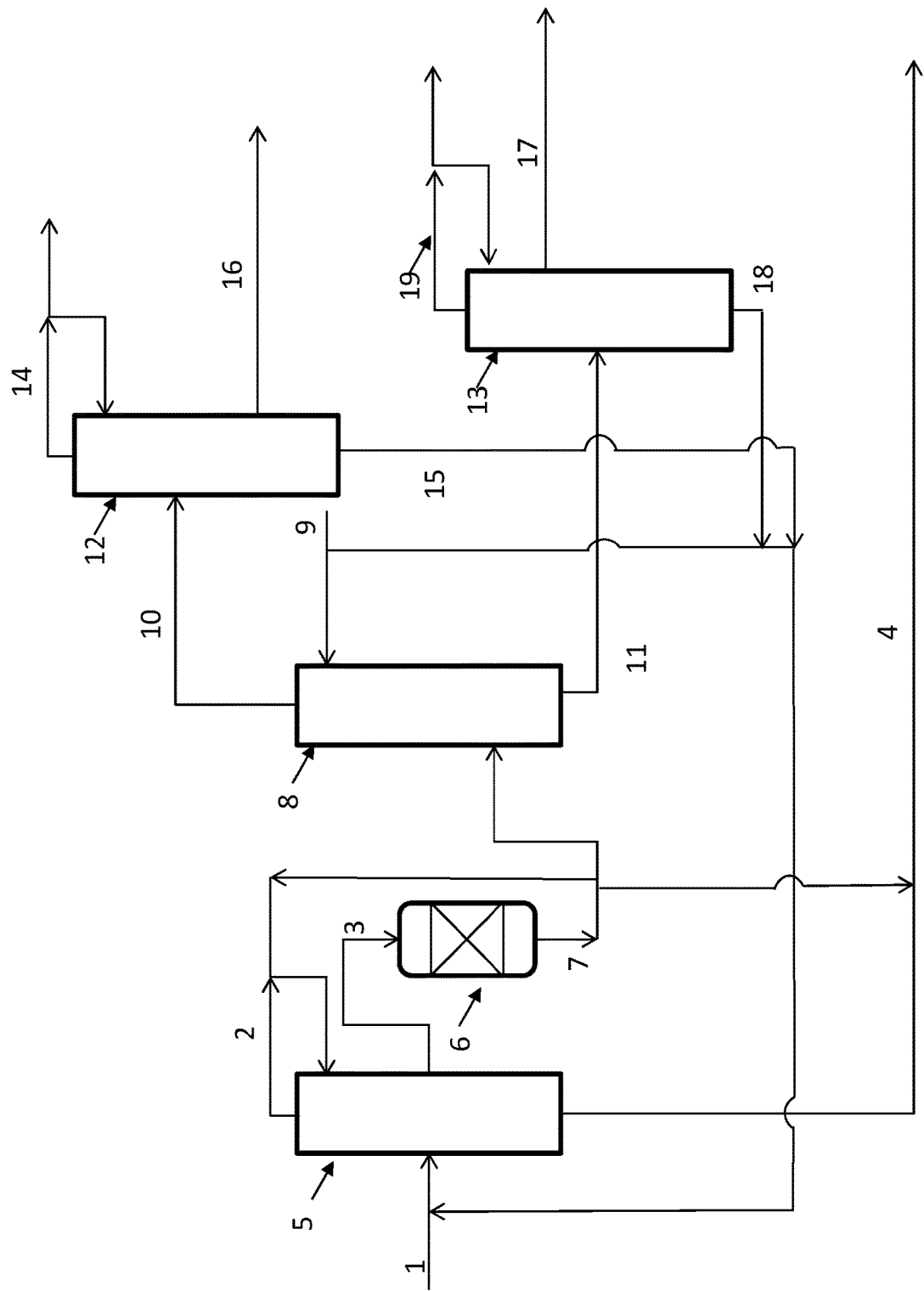
FIG. 1 is a simplified process flow diagram of a process for an integrated reactor system according to embodiments disclosed herein.

In one aspect, methods and systems for producing high purity methanol from crude MTBE feed using one or multiple divided wall columns are provided. The method can include purifying the MTBE, dissociating the MTBE to produce isobutene and methanol, purifying the isobutene and recovering/purifying methanol.

Divided wall columns herein may be used to separate multicomponent mixtures into pure fractions. They are particularly suited to obtain high purity medium boiling fractions. The separation of a three-component mixture into its fractions in conventional distillation systems requires a sequential system with at least two columns or main columns with side columns. With a divided wall column, only one fractionator is used to separate lights and heavies from the medium boiling point product. A vertical wall is introduced in the middle part of the column, creating a feed and draw-off section in this part of the column. This arrangement saves a second column. The column shell, internals, reboiler and condenser for a second column are not needed.

As used herein, the term "divided wall column" refers to any column having a dividing wall suitable for the separation of a mixture containing two or more components having differing boiling points. As used herein, the term "dividing wall" refers to any partition disposed at least partially within an interior of a column to provide at least a first fractionation zone on one side of the dividing wall and a second fractionation zone on the other side of the dividing wall. The dividing wall can be either segmented or continuous. The dividing wall can be parallel or non-parallel relative to a longitudinal axis of the column. The first fractionation zone and the second fractionation zone can have the same or different cross-sectional areas and/or volumes. The column can have a circular cross-section and the dividing wall can positioned or disposed within the column to provide the first fractionation zone and the second fractionation zone having equal or un-equal cross-sectional areas with respect to one another. The dividing wall can extend completely or only partially from one side of the dividing wall column to the other side of the dividing wall column.

A divided wall column according to embodiments herein is, in principle, a system of thermally coupled distillation columns. In divided wall columns herein, a dividing wall is located in the interior space of the column. Divided wall columns herein may use a chord wall or an annular wall. The dividing wall generally is vertical. Two different mass transfer separations occur on either side of the dividing wall, which may have different operating pressures and temperatures, the dividing wall may have to withstand a pressure differential and/or a temperature differential across the dividing wall.

Divided wall columns herein may include internals which comprise trays, rotating trays, random and/or structured packings. Useful column trays include the following types: trays having drillholes or slots in the tray plate; trays having throats or chimneys which are covered by bubble-caps, caps or hoods; trays having drillholes in the tray plate which are covered by movable valves; trays having special constructions. In columns having rotating internals, the reflux is either sprayed by rotating funnels or distributed as a film onto a heated tube wall with the aid of a rotor. Columns may comprise random packings of various shaped bodies.

The divided wall columns may have common stripping and rectification sections with the divided wall being located in the middle. Such a design allows for effecting different vapor and liquid travel on either side of the wall, thus increasing product purity while minimizing equipment unit count.

A methanol feed, for example, may be processed according to embodiments herein to produce the highest methanol concentration within the divided wall column while minimizing the amount of methanol leaving with the bottoms product. This results in close to the azeotropic concentration in the distillate product and in the distillation zone. The methanol must be separated from the hydrocarbons so that the hydrocarbons may be used for gasoline blending and to conserve methanol. The separation may be achieved by washing the hydrocarbon/methanol mixture with water. The methanol may be selectively absorbed in the water phase, which is subsequently fractionated to separate the methanol.

The divided wall column, according to one or more embodiments disclosed herein, may be used in an existing integrated MTBE and isobutene facility, for example, and may produce high purity isobutene only. The existing facility may have all the methanol produced from the isobutene unit being recycled to the MTBE unit. In order to process additional import MTBE and to make export quality commercial grade methanol at the same time, a new methanol purification section would need to be installed in such a facility. Such a methanol purification section may need to have two distillation columns (methanol topping and methanol tailing columns) with associated equipment. The divided wall column disclosed herein may be used instead of multiple separate traditional, columns for the production of commercial grade methanol.

Additionally, the integrated MTBE and isobutene process may not have the flexibility to produce commercial grade methanol. In order to co-produce methanol by including additional MTBE import in the isobutene section, a methanol purification section may need to be integrated in the process. This methanol purification process may involve a dividing wall column, or a series of distillation columns, to achieve an on-specification methanol product while using minimal pieces of equipment. Additionally, the reboiling/condensing duty of the process may be around 30% lower than a two column conventional system. Finally, as the divided wall column may use less equipment, there is a significant saving in required plot area and structure (pipe rack, foundation, etc.).

According to one or more embodiments disclosed herein is a divided wall column, or series of distillation columns, which may take the bottoms of an extraction column and separate out one or more of MTBE, DIB, TBA, DME, MSBE, TAME, and water from the methanol to make an export grade methanol product.

The method to produce high purity isobutene will now be described with reference to FIG. 1. To purify the MTBE, crude MTBE 1 is introduced into a fractionation column 5. Crude MTBE 1 may be obtained from isobutenic C4 olefin mixtures, for example from the C4 cut from steam crackers or FCC units. The crude MTBE may also include methanol, secondary butyl alcohol (SBA), tert-butyl alcohol (TBA), 2-methoxybutane (MSBE), diisobutene, tertiary amyl methyl ether (TAME) and other high boiling point components.

In some embodiments, the crude MTBE stream 1 may include a 94-97 wt % MTBE stream, such as a 95.9 wt. % MTBE. The crude MTBE stream 1 may also contain small amounts of highly unsaturated compounds such as 1,3-butadiene, trans-1,3-pentadiene, cis-1,3-pentadiene, 2-methyl-1,3-butadiene, and others. The feed stream may additionally comprise crude MTBE provided from an upstream etherification reaction zone and a supplemental MTBE feed stream. Such supplemental MTBE feed stream may come from a separate facility, OSBL, an upstream separation system, or other sources.

The MTBE stream 1 can be introduced at an intermediate point in the column 5. A light hydrocarbon stream 2 can be withdrawn from the column 5 at or proximal the first end thereof and a side-stream 3 can be withdrawn from an intermediate point in the column 5. The light hydrocarbon stream 2 may be recycled to the top of the column 5 as a reflux. The light hydrocarbon stream 2 may be a mixture of MTBE, methanol, water, and highly unsaturated compounds. The side-stream may be an MTBE stream of increased purity as compared to the MTBE feed stream 1. The side stream may further include one or more impurities present in the feed stream. A heavy hydrocarbon stream 4 can be withdrawn from the divided wall column 5 at or proximal the lower end thereof. The heavy hydrocarbon 4 may be a mixture of MTBE, tert-butyl alcohol (TBA), 2-methoxybutane (MSBE) and higher olefins.

The fractionation column 5 may operate at temperatures ranging from about 45° C. to about 130° C. and pressures ranging from about 0.1 to about 5 barg. The purification of MTBE 1 provides the sidestream (MTBE) 3 having a composition such as about 99.5 wt % MTBE or greater, such as 99.8 wt % MTBE or 99.9 wt % MTBE. The MTBE side stream may be produced by fractional distillation in the fraction system 5, separating the MTBE 1 into the light hydrocarbons 2 comprising MTBE, methanol, water and other low boiling components, and the heavy hydrocarbons 4 comprising butene oligomers, TBA, and other high boiling components, while withdrawing the high purity MTBE sidestream 3.

To produce isobutene, the MTBE sidestream 3 may be sent to a reactor 6 to produce isobutene. The reactor 6 dissociates the high purity MTBE 3 and produces a raw isobutene stream 7 comprising isobutene, methanol and unreacted MTBE. In some embodiments, the reactor 6 includes a fixed bed operating at reaction bed temperatures ranging from about 90° C. to about 160° C., in other embodiments from about 120° C. to about 150° C. The high purity MTBE 3 may be fed at an inlet temperature of about 110° C. to about 150° C. in some embodiments, about 115° C. to about 145° C. in other embodiments. The reactor 6 may have an LHSV (liquid hourly space velocity) ranging from about 7 to about 35, or from about 10 to about 30, or from about 14 to about 25. The reactor 6 may have a pressure drop through said fixed bed in the range of about 0.5 to about 50 psig and at a reaction pressure ranging from about 0.5 to about 4 atmospheres.

The raw isobutene stream 7 is sent for product purification. The raw isobutene 7 may be sent to an extraction column 8 to extract methanol and unreacted MTBE from isobutene. The extraction column 8 uses an extractant 9 fed in a countercurrent fashion to the raw isobutene 7 thereby producing a washed reactor effluent 10 as an overhead and a bottoms product 11. The washed reactor effluent 10, which may include isobutene, MTBE, and residual light components, may be fed to an isobutene fractionation system 12 and the bottoms product 11, which may include water, methanol, MTBE, and residual heavy components, may be fed to a methanol fractionation system 13. The extractant 9 may be water or another suitable extractant useful to separate methanol from isobutene.

In various embodiments, at least a portion of the raw isobutene 7 may be recycled to the first fraction system 5 as additional reflux, collected as product, and/or combined with the heavy hydrocarbons 4 and sent offsite as byproduct.

To recover the isobutene, the method may include introducing the washed reactor effluent 10 to an isobutene fractionation system 12, similar to that as described above for the purification of the MTBE. The washed reactor effluent 10 may be introduced at an intermediate point of the isobutene fractionation column 12. A light ends overhead 14 can be withdrawn from the isobutene fractionation column 12 at or proximal the upper end thereof and may be vented or recycled to the isobutene fractionation system 12 as reflux. A side-stream of high purity isobutene 16 can be withdrawn from an intermediate point of the isobutene fractionation column 12, which may be used in downstream processes, or may be recovered as a product and sent offsite. Such high purity isobutene stream may have a purity of 95 wt %, 97 wt %, 98 wt %, 99 wt %, 99.5 wt %, 99.6 wt %, 99.7 wt %, 99.8 wt %, or even 99.85 wt % isobutene. The isobutene column 12 may also produce a bottom product 15, which may be a mixture of isobutene, MTBE and/or water which may be recycled to fractionation system 5. The isobutene column 12 may operate at temperatures ranging from about 45° C. to about 150° C. and pressures ranging from about 3 to about 15 barg.

To recover/purify a methanol product stream, the bottoms product 11 from the extraction column 8 may be fed to an intermediate point of the methanol fractionation system 13. The methanol fractionation system may a series of fractionation columns such a methanol toppings column followed by a methanol bottoms bottom column, or may be a divided wall column as will be described below. The methanol fraction system 13 may provide a high purity methanol product 17 withdrawn as a sidestream from an intermediate point of the methanol column 13, a bottoms stream 18, and an overhead stream 19. The light overhead stream 19 may comprise methanol and other light components and may be vented or recycled to the methanol fractionation system 13 as reflux. The bottoms 18 may include water, TBA, MTBE and/or methanol. The bottoms 18 may be recycled to either the extraction column 8 or the fractionation system 5. The methanol column 13 may operate at temperatures ranging from about 45° C. to about 180° C. and pressures ranging from about 01 to about 5 barg.

Figure 2:
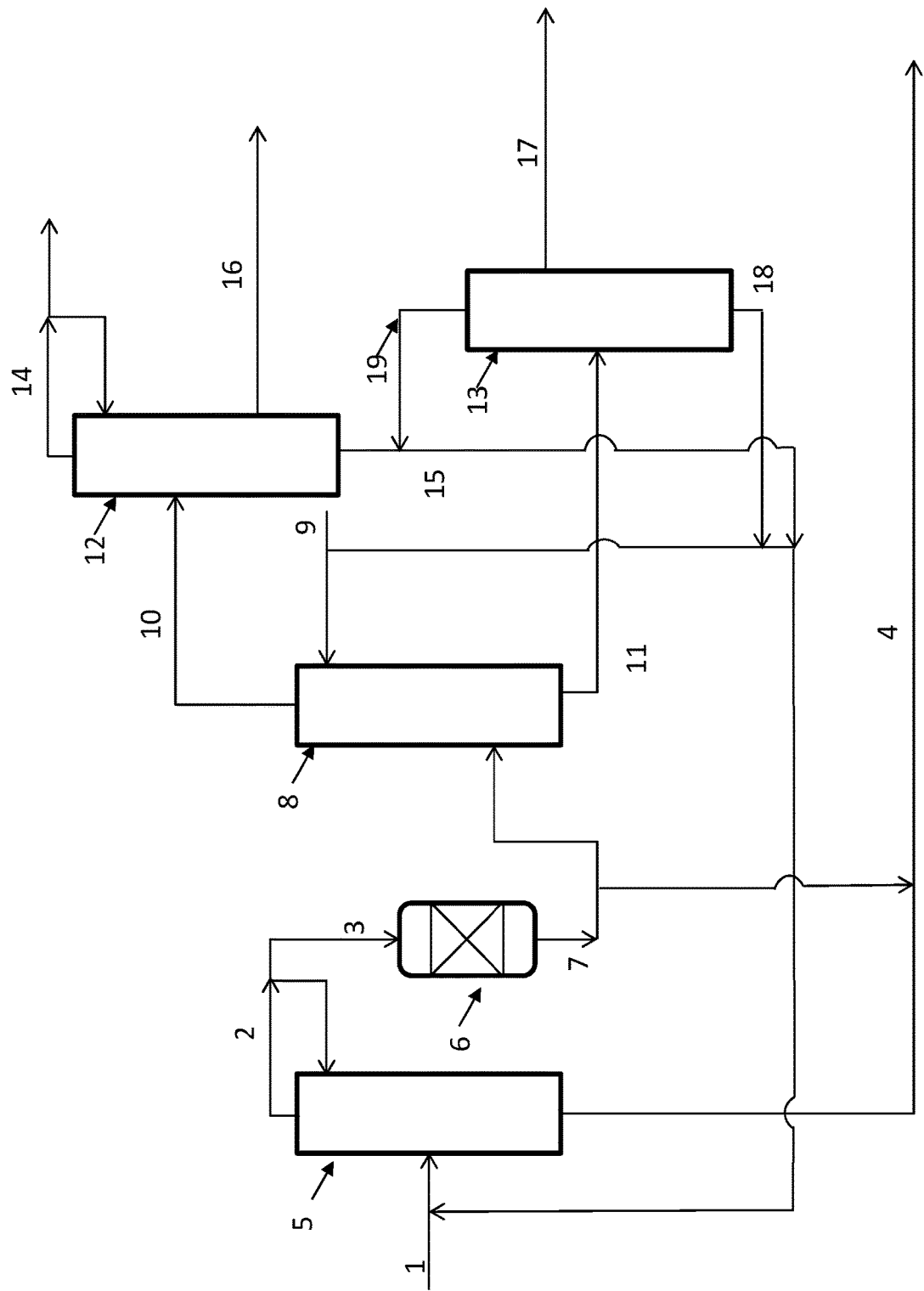
FIG. 2 is a simplified process flow diagram of a process for an integrated reactor system according to embodiments disclosed herein.

In about embodiments disclosed herein, as illustrated in FIG. 2, the first fraction system 5 may recover MTBE in the overhead products. The overall process scheme will proceed similarly, with residual MTBE, water, and isobutene being recycled in bottoms stream 15. Additionally, methanol, residual isobutene, and other light components may be recycled to the first fraction system via flowline 19.

The overall processing schemes disclosed herein may be performed using single fraction columns, a series of fraction columns, or divided wall columns. Resulting advantages of using divided wall columns may include: reduced capital investment; and elimination or significant reduction in the need for multiple columns to provide the same level of purity of products, among other advantages.

In one aspect, embodiments herein relate to the use of a dividing wall distillation column. The feed to the dividing wall column may be from a prior column or reactor in which less than all of the reactants were reacted. The feed material contains the reactants and product which is fed to a pre-fraction section of the dividing wall column. A post-fraction section then produces the methanol product as a side draw. Between the pre- and post-fractionation sections is a common bottoms section that recovers as much methanol as possible while concentrating the water and TBA into the bottoms product. The overhead of the column serves to reflux the pre-fractionation section, acts as the feed/reflux to the post-fractionation section, and a portion is drawn as the overheads product that may be sent back to an MTBE synthesis section. Makeup material may be added as required. There may be a common stripping section below the divided vertical section.

The pre-fractionation section is responsible for separating methanol/MTBE from water and TBA. This section may be refluxed such that a separation is made between the methanol and the water/TBA. The post-fractionation section of the dividing wall column may separate the MTBE from a portion of the methanol. And, a side draw may draw the methanol product from the post-fractionation section. Sufficient reflux may be sent to this section to maximize the recovery of methanol, while minimizing the amount of impurities, in the side draw product. The section of the column below the dividing wall may include sufficient mass transfer packing or catalyst to further recover methanol from water/TBA exiting the bottom of the pre-fractionation section. The liquid coming from the pre- and post-fractionation sections and collecting in the common bottoms section serves as the internal reflux for this portion of the column.

Further, the ancillary equipment for this tower may be similar to that as used on any distillation column. For example, the system may include a common overhead system, recovering the overhead from each of the pre- and post-fractionation sections of the dividing wall column. The condenser may be a total condenser which condenses the vapor coming from the pre- and post-fractionation sections. The condensed overhead may then be directed to a reflux accumulator, or overhead drum, the effluent of which may be split between the overhead product and the reflux for the tower. The reflux may be fed to the pre-fractionation, the post-fractionation, or both, in equal or unequal amounts, depending on the column separation dynamics. The column may use a single, common reboiler to provide the required boil-up for the separation.

Additionally, the product stream drawn from the side draw may be fed to a product cooler which brings the methanol to transport temperatures.

According to one or more embodiments disclosed herein, the distillation column may have at least two vertical distillation sections, including a pre-fraction section with the inlet feed, and a post-fraction section with a side draw. The dividing wall column may also have at least one wall separating the at least two vertical distillation sections. The wall may extend through a vertical portion of the distillation column, the wall extending less than the total height of the column. The dividing wall column may also be equipped with a common stripping section below the at least two vertical distillation sections. The common stripping section may be in fluid communication around the bottom vertical terminus of the wall. The wall extending through the vertical portion of the distillation column may extend from the top of the column to about the top of the stripping section.

Additionally, the dividing wall column may have a common overhead condenser system. The common overhead condenser system may receive an overhead product from the at least two vertical distillation sections, and may feed the overheads to a common overheads drum. The common overheads drum may be equipped with all the necessary piping and valving to recycle a condensed overhead product each of the at least two vertical distillation sections.

The pre- and post-fraction sections may be located completely, or partially, in the rectification section of the distillation column. The dividing wall column may use a side draw located in the rectification section of the post-fraction section and may be configured for product recovery. Additionally, the dividing wall column may use a common bottoms reboiler, which may provide the entire heating duty for boil-up and a separate bottoms product stream. The overheads drum may also have an overhead products stream.

Figure 3:
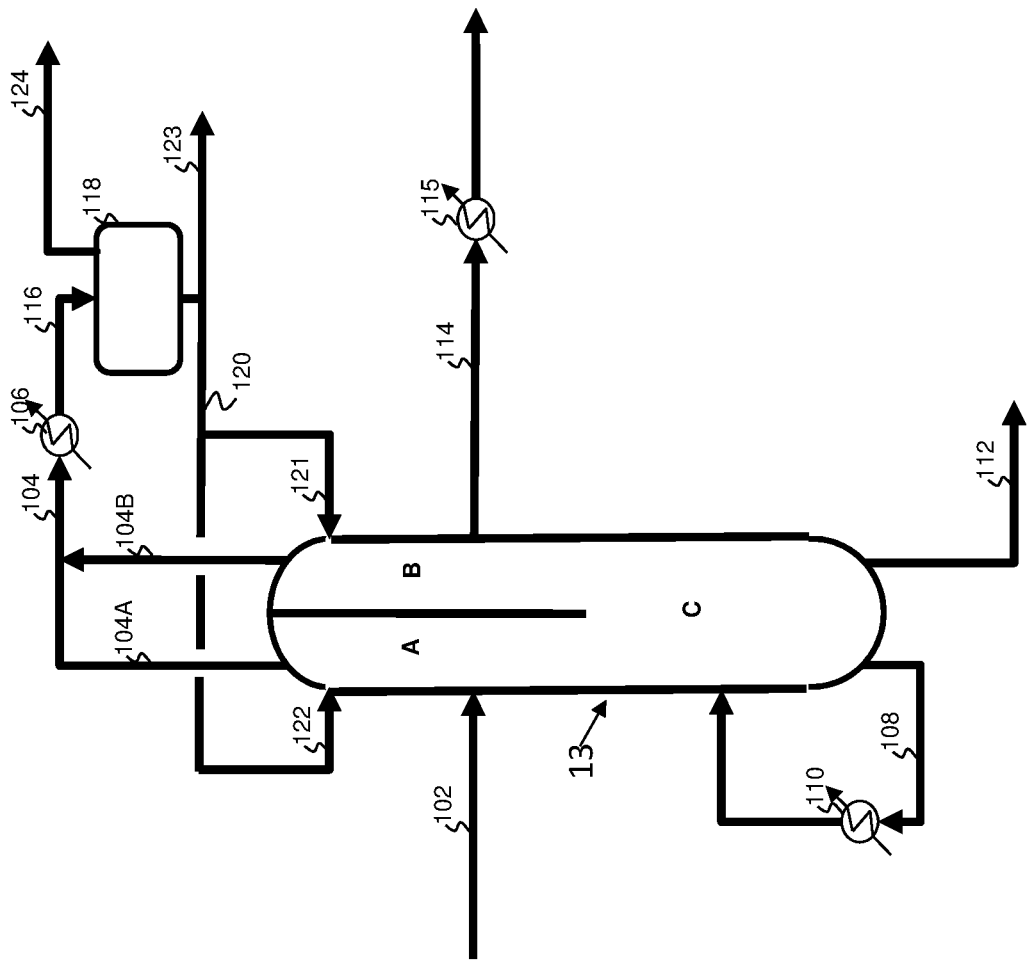
FIG. 3 is an illustration of a divided wall column according to embodiments disclosed herein.

Referring now to FIG. 3, a methanol purification process may be carried out in the dividing wall column and may operate generally as follows.

Feedstock 102, which may include one or more of MTBE, DIB, TBA, DME, MSBE, TAME, water, and methanol, is fed to pre-fractionation section A. As illustrated, pre-fractionation section A may separate one or more feed components to produce methanol. Liquid travels down the dividing wall column and into the common stripping section C. Vapor exits the top of the section A by overheads stream 104A and enters the common overheads condenser 106.

A first portion of the liquids in the commons stripping section C is fed to the common reboiler 110 through a first bottoms outlet 108. A second portion of the liquids in the common stripping section C is recovered by outlet 112. Both portions may include water, TBA, other heavy components, and some residual methanol. The vapor portion traveling upwards out of commons stripping section C may flow into the pre-fractionation section A and the post-fractionation section B.

In all cases, the vapor traveling upwards in the column may be purposely divided at the lowermost terminus of the dividing wall in a prescribed ratio as determined beforehand from rigorous reactive-distillation simulation of the divided-wall configuration. Such division of flow may be controlled to prescribed values by engineering-design methods incorporating either active or passive means. Again, such division of flow may held at prescribed values using engineering design methods incorporating either active or passive means. Such means include having a larger bottom opening on section A or section B, the dividing wall being off-center, or the amount of reflux being fed to section A or section B.

The post-fractionation section B may include the product side draw 114. The side draw product may be substantially pure methanol. As defined herein, substantially pure may be a purity of at least 95 wt %, 97 wt %, 98 wt %, 99 wt %, 99.5 wt %, 99.6 wt %, 99.7 wt %, 99.8 wt %, or even 99.85 wt %. The product methanol may be fed through a product cooler 115 to be prepared for transport.

As with the pre-fractionation section, the post-fractionation section B may separate one or more feed components to produce methanol. Liquid travels down the dividing wall column and into the common stripping section C. Vapor exits the top of the section B by overheads stream 104B and enters the common overheads condenser 106. Overhead streams 104A and 104B are combined into a common overheads stream 104.

The combined, condensed overheads 116 may be fed to an overheads collection drum 118. A vapor portion 124 exiting the overheads drum may be used to un-deadhead the column and increase vapor travel through sections A, B, and C. The vapor portion 124 may be recycled to upstream processes, or downstream processes, or flared, as necessary.

A liquid portion 120 exiting the overheads collection drum 118 may be fed, as reflux, to post-fractionation section B via stream 121, pre-fractionation section A via stream 122, or both. A portion of the liquid portion 120 which is not fed as reflux may be recovered via stream 123 and recycled to upstream processes, downstream process, or flared, as necessary.

The division of the reflux as to how much goes to zone A versus how much goes to zone B may be intentionally designed for and may be controlled. Appropriate valving may be used to vary the amount of reflux fed to zone A or zone B at any given time. For example, the dividing wall column may be operated such that no vapor portion 124 is removed, and the totality of the reflux may be fed to either zone A or zone B. Alternatively, the dividing wall column may be operated such that no vapor portion 124 is removed, and the totality of the reflux may be fed to zone A and zone B in equal, or unequal, amounts. Alternatively, the dividing wall column may be operated such that vapor portion 124 is removed, and the totality of the liquid reflux may be fed to either zone A or zone B. Or alternatively, the dividing wall column may be operated such that vapor portion 124 is removed, and the totality of the liquid reflux may be fed to zone A and zone B in equal, or unequal, amounts.

In one or more embodiments herein, the light components may be concentrated and purged as overhead product. Purging of lights is needed to control temperatures in catalytic distillation columns.

Section A parallels section B and is fed via liquid reflux from the overhead condenser system and vapor from stripping section C and the reboiler. The split of the vapor between section A and section B may be intentionally controlled at prescribed levels using either active or passive engineering-design means.

In another embodiment disclosed herein, the distillation column may have at least two vertical distillation sections, including a pre-fraction section with the inlet feed, and a post-fractionation section with a side draw. The dividing wall column may also have at least one wall separating the at least two vertical distillation sections. The wall may extend through a mid portion of the distillation column, the wall extending less than the total height of the column. The dividing wall column may also be equipped with a common stripping section below the at least two vertical distillation sections. The common stripping section may be in fluid communication around the bottom vertical terminus of the wall.

Additionally, the dividing wall column may have a common overhead condenser system. The common overhead condenser system may receive an overhead product from the at least two vertical distillation sections, and may feed the overheads to a common overheads drum. The common overheads drum may be equipped with all the necessary piping and valving to recycle a condensed overhead product to the top tray of each of the at least two vertical distillation sections.

The pre- and post-fraction sections may be located completely, or partially, in the rectification section of the distillation column. The dividing wall column may use a side draw located in the rectification section of the post-fraction section and may be configured for product recovery. Additionally, the dividing wall column may use a common bottoms reboiler, which may provide the entire heating duty for boil-up and a separate bottoms product stream. The overheads drum may also have an overhead products stream.

Figure 4:
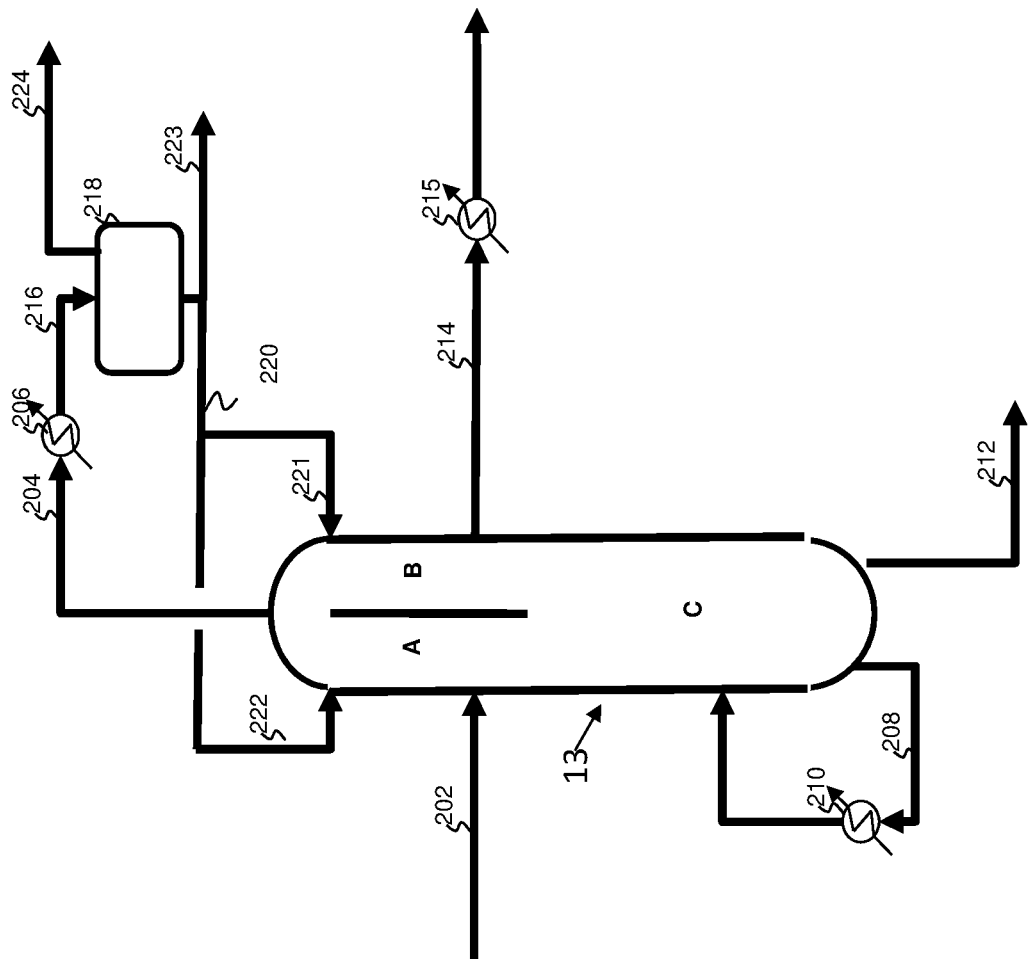
FIG. 4 is an illustration of a divided wall column according to embodiments disclosed herein.

Referring now to FIG. 4, a methanol purification process may be carried out in the dividing wall column and may operate generally as follows.

Feedstock 202, which may include one or more of MTBE, DIB, TBA, DME, MSBE, TAME, water, and methanol, is fed to pre-fractionation section A. As illustrated, pre-fractionation section A may separate one or more feed components to produce methanol. Liquid travels down the dividing wall column and into the common stripping section C. Vapor exits the top of the section A by overheads stream 204 and enters the common overheads condenser 206.

A first portion of the liquids in the commons stripping section C is fed to the common reboiler 210 through a first bottoms outlet 208. A second portion of the liquids in the common stripping section C is recovered by outlet 212. Both portions may be water, TBA, other heavy components, and some residual methanol. The vapor portion travel upwards out of commons stripping section C may flow into the pre-fractionation section A and the post-fractionation section B.

In all cases, the vapor traveling upwards in the column may be purposely divided at the lowermost terminus of the dividing wall in a prescribed ratio as determined beforehand from rigorous reactive-distillation simulation of divided-wall configuration. Such division of flow may be controlled to prescribed values by engineering-design methods incorporating either active or passive means. Again, such division of flow may held at prescribed values using engineering design methods incorporating either active or passive means. Such means include having a larger bottom opening on section A or section B, the dividing wall being off-center, or the amount of reflux being fed to section A or section B.

The post-fractionation section B may include the product side draw 214. The side draw product may be substantially pure methanol. As defined herein, substantially pure may be a purity of at least 95 wt %, 97 wt %, 98 wt %, 99 wt %, 99.5 wt %, 99.6 wt %, 99.7 wt %, 99.8 wt %, or even 99.85 wt %. The product methanol may be fed through a product cooler 215 to be prepared for transport.

As with the pre-fractionation section, the post-fractionation section B may separate one or more feed components to produce methanol. Liquid travels down the dividing wall column and into the common stripping section C. Vapor exits the top of the section B by overheads stream 204 and enters the common overheads condenser 206.

The combined, condensed overheads 216 may be fed to an overheads collection drum 218. A vapor portion 224 exiting the overheads drum may be used to un-deadhead the column and increase vapor travel through sections A, B, and C. The vapor portion 224 may be recycled to upstream processes, or downstream processes, or flared, as necessary.

A liquid portion 220 exiting the overheads collection drum 218 may be fed, as reflux, to an area approximate the top tray in post-fractionation section B via stream 221, to area approximate the top tray in pre-fractionation section A via stream 222, or both. A portion of the liquid portion 220 which is not fed as reflux may be recovered via stream 223 and recycled to upstream processes, downstream process, or flared, as necessary.

The division of the reflux as to how much goes to zone A versus how much goes to zone B may be intentionally designed for and may be controlled. Appropriate valving may be used to vary the amount of reflux fed to zone A or zone B at any given time. For example, the dividing wall column may be operated such that no vapor portion 224 is removed, and the totality of the reflux may be fed to either zone A or zone B. Alternatively, the dividing wall column may be operated such that no vapor portion 224 is removed, and the totality of the reflux may be fed to zone A and zone B in equal, or unequal, amounts. Alternatively, the dividing wall column may be operated such that vapor portion 224 is removed, and the totality of the liquid reflux may be fed to either zone A or zone B. Or alternatively, the dividing wall column may be operated such that vapor portion 224 is removed, and the totality of the liquid reflux may be fed to zone A and zone B in equal, or unequal, amounts.

In one or more embodiments herein, the light components may be concentrated and purged as overhead product. Purging of lights is needed to control temperatures in catalytic distillation columns.

Section A parallels section B and is fed via liquid reflux from the overhead condenser system and vapor from stripping section C and the reboiler. The split of the vapor between section A and section B may be intentionally controlled at prescribed levels using either active or passive engineering-design means. Control of reflux to section A and section B may be above the top tray for each section or may be controlled by internals within the column.

In a conventional distillation column reactor there is generally a reflux of condensed overheads to facilitate the separation of the more volatile unreacted components from the product. In the case of purification of methanol, the overheads may contain methanol, and other lighter materials which might be in the feed. The condensable overheads are recovered and the methanol may be separated from the hydrocarbons by water washing, the methanol being selectively removed in the water phase. The methanol and water may then be refluxed and the methanol further separator in the distillation column.

Further, in other embodiments, the methanol distillation column may be a series of distillation columns operated in parallel such that a high purity methanol stream may be obtained.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process for the coproduction of isobutene and high purity methanol, the process comprising:
   a. separating a feed stream comprising crude methyl tertiary butyl ether (MTBE) in a first fractionation system to recover an MTBE product stream comprising at least 94 wt % MTBE, and to recover a heavies stream;
   b. contacting the MTBE product stream with a catalyst to provide an effluent comprising isobutene and methanol;
   c. contacting the effluent comprising isobutene and methanol with one or more extractants to produce an extractant/methanol stream and a mixed isobutene stream;
   d. feeding the mixed isobutene stream into a second fractionation system to recover a stream comprising isobutene comprising at least 95 wt % isobutene;
   e. feeding the extractant/methanol stream into a third fractionation system comprising a divided wall distillation column to recover a lights fraction, a methanol product stream comprising at least 95 wt % methanol and a heavies fraction comprising the extractant; and
   recycling at least a portion of the lights fraction from the third fractionation system to the first fractionation system.

2. The process of claim 1, wherein the feed stream comprises crude MTBE provided from an etherification reaction zone and a supplemental MTBE feed stream.

3. The process of claim 2, further comprising feeding the lights fraction from the third fractionation system to the etherification reaction zone.

4. The process of claim 1, wherein the feed stream further comprises diisobutene (DIB), tertiary butyl alcohol (TBA) and 2-methoxybutane (MSBE).

5. The process of claim 1, wherein the extractant comprises water.

6. The process of claim 1, wherein the first, second, and third fractionation systems each comprise a divided wall distillation column.

7. The process of claim 1, further comprising removing a stream comprising MTBE/isobutene from the second fractionation system.

8. The process of claim 7, further comprising recycling the MTBE/isobutene to the first fractionation system.

9. The process of claim 1, wherein the methanol stream comprises at least 99.8 wt % methanol.

10. A process for the coproduction of isobutene and high purity methanol, the process comprising:
    a. separating a feed stream comprising crude methyl tertiary butyl ether (MTBE) in a first fractionation system to recover an MTBE product stream comprising at least 94 wt % MTBE, and to recover a heavies stream;
    b. contacting the MTBE product stream with a catalyst to provide an effluent comprising isobutene and methanol;
    c. contacting the effluent with one or more extractants to produce an extractant/methanol stream and a mixed isobutene stream;
    d. feeding the mixed isobutene stream into a second fractionation system to recover a stream comprising isobutene and comprising at least 95 wt % isobutene;
    e. feeding the extractant/methanol stream into a third fractionation system comprising a divided wall distillation column to recover an overheads fraction, a methanol side draw product stream comprising at least 95 wt % methanol and a bottoms stream comprising the extractant.

11. The process of claim 10, further comprising removing a stream comprising MTBE/isobutene from the second fractionation system.

12. The process of claim 11, further comprising recycling the MTBE/isobutene to the first fractionation system.

13. The process of claim 10, further comprising recycling at least a portion of the lights fraction from the third fractionation system to the first fractionation column.

14. A process for the coproduction of isobutene and high purity methanol, the process comprising:
    a. separating a feed stream comprising crude methyl tertiary butyl ether (MTBE), diisobutene (DIB), tertiary butyl alcohol (TBA) and 2-methoxybutane (MSBE) in a first fractionation system to recover an MTBE product stream comprising at least 94 wt % MTBE, and to recover a heavies stream comprising a mixture of MTBE, tert-butyl alcohol (TBA), and 2-methoxybutane (MSBE);

b. contacting the MTBE product stream with a catalyst to provide an effluent comprising isobutene, methanol, and residual MTBE;
c. contacting the effluent with one or more extractants to produce an extractant/methanol stream and a mixed isobutene/MTBE stream;
d. feeding the mixed isobutene/MTBE stream into a second fractionation system to recover a stream comprising isobutene comprising at least 94 wt % isobutene and a heavies stream comprising MTBE/isobutene;
e. recycling the heavies stream comprising MTBE/isobutene to the first fractionation system;
f. feeding the extractant/methanol stream into a third fractionation system comprising a divided wall distillation column to recover an overheads fraction, a methanol side draw product stream comprising at least 95 wt % methanol and a bottoms stream comprising residual MTBE, methanol, and the extractant; and
g. recycling the bottoms stream comprising residual MTBE, methanol, and the extractant to the first fractionation system.

\* \* \* \* \*